(12) United States Patent
Li et al.

(10) Patent No.: US 9,585,653 B2
(45) Date of Patent: Mar. 7, 2017

(54) TISSUE FIXATION DEVICES AND METHODS

(75) Inventors: Jamie Li, Lexington, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 612 days.

(21) Appl. No.: 13/610,298

(22) Filed: Sep. 11, 2012

(65) Prior Publication Data

US 2013/0079813 A1     Mar. 28, 2013

Related U.S. Application Data

(60) Provisional application No. 61/537,861, filed on Sep. 22, 2011.

(51) Int. Cl.

| | | |
|---|---|---|
| *A61B 17/08* | (2006.01) | |
| *A61B 17/06* | (2006.01) | |
| *A61B 17/04* | (2006.01) | |
| *A61B 17/064* | (2006.01) | |
| *A61B 17/068* | (2006.01) | |
| *A61B 17/00* | (2006.01) | |
| *A61F 2/00* | (2006.01) | |

(52) U.S. Cl.
CPC ........ *A61B 17/06109* (2013.01); *A61B 17/04* (2013.01); *A61B 17/0401* (2013.01); *A61B 17/0469* (2013.01); *A61B 17/064* (2013.01); *A61B 17/0682* (2013.01); *A61B 2017/00805* (2013.01); *A61B 2017/0419* (2013.01); *A61B 2017/061* (2013.01); *A61F 2/0045* (2013.01)

(58) Field of Classification Search
CPC . A61B 17/04; A61B 17/0401; A61B 17/0469; A61B 17/064
See application file for complete search history.

(56) References Cited

U.S. PATENT DOCUMENTS

2003/0236535 A1    12/2003   Onuki et al.
2008/0065120 A1    3/2008   Zannis et al.
(Continued)

FOREIGN PATENT DOCUMENTS

| WO | 00/49950 A1 | 8/2000 |
|---|---|---|
| WO | 2013/043431 A1 | 3/2013 |

OTHER PUBLICATIONS

International Search Report and Written Opinion for PCT Patent Application No. PCT/US2012/054851, mailed on Nov. 26, 2012, 20 pages.

(Continued)

*Primary Examiner* — Robert Lynch
(74) *Attorney, Agent, or Firm* — Brake Hughes Bellermann LLP

(57) ABSTRACT

In one embodiment, a medical device includes a tissue anchor, and elongate member, a first needle, and a second needle. The tissue anchor has a first arm portion, a second arm portion, and a base portion extending between the first arm portion and the second arm portion. The first needle extends from the elongate member. The first needle defines a lumen configured to receive the anchor member of the first arm portion of the tissue anchor. The second needle extends from the elongate member. The second needle defines a lumen configured to receive the anchor member of the second arm portion of the tissue anchor.

18 Claims, 9 Drawing Sheets

(56) References Cited

U.S. PATENT DOCUMENTS

2009/0118734 A1  5/2009 Bhatnagar et al.
2010/0030016 A1  2/2010 Knoll
2010/0094425 A1* 4/2010 Bentley .............. A61B 17/0482
                                                      623/17.16

OTHER PUBLICATIONS

International Preliminary Report on Patentability for PCT Patent Application No. PCT/US2012/054851, mailed on Apr. 3, 2014, 9 pages.

* cited by examiner

TISSUE FIXATION DEVICES AND METHODS

CROSS-REFERENCE TO RELATED APPLICATION

This application is a Nonprovisional of, and claims priority to, U.S. Patent Application No. 61/537,861, filed Sep. 22, 2011, entitled "TISSUE FIXATION DEVICES AND METHODS", which is incorporated by reference herein in its entirety.

TECHNICAL FIELD

This disclosure relates generally to medical devices and more particularly to medical devices that include fixation devices or tissue anchors.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Some such medical procedures include placing a support member or implant into the body of the patient such that the support member or implant provides support to a portion of the body of the patient. Specifically, in some medical procedures, the support member or implant may be fixed or coupled to the body of the patient at various locations within the body of the patient and a support portion of the support member or implant may be placed beneath the portion of the body to be supported.

In some known medical procedures, tissue anchors or fixation devices are used fix or couple portions of the support member to portions of the body of the patient. A need exists for a tool or medical device that is configured to effectively place fixation or tissue anchors inside the body of the patient. A need also exists for fixation devices or tissue anchors that may be coupled to or provide support for various portions of a bodily implant.

SUMMARY

In one embodiment, a medical device includes a tissue anchor, and elongate member, a first needle, and a second needle. The tissue anchor has a first arm portion, a second arm portion, and a base portion extending between the first arm portion and the second arm portion. The first needle extends from the elongate member. The first needle defines a lumen configured to receive the anchor member of the first arm portion of the tissue anchor. The second needle extends from the elongate member. The second needle defines a lumen configured to receive the anchor member of the second arm portion of the tissue anchor.

In another embodiment, a method includes disposing a tissue anchor into bodily tissue of a patient, the tissue anchor having a first arm portion, a second arm portion, and a base portion disposed between the first arm portion and the second arm portion; coupling a first suture to the tissue anchor; and coupling a second suture to the tissue anchor.

In yet another embodiment, a method includes disposing a tissue anchor into bodily tissue of a patient, the tissue anchor having a first arm portion, a second arm portion, and a base portion disposed between the first arm portion and the second arm portion; coupling a first suture to the tissue anchor; and coupling a second suture to the tissue anchor.

DETAILED DESCRIPTION

The devices and methods described herein are generally directed to procedures for placing implants within a body of a patient. In some embodiments, the implants are pelvic implants (e.g., posterior support implants, anterior support implants, total pelvic floor repair implants) and the delivery and placement of such implants within a pelvic region (also referred to herein as "pelvis") of a patient. An implant can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. A single implant or multiple implants can be used in a single procedure. In some applications, when multiple implants are used, support can be provided in desired areas and improved control of the direction of stretch or support of the implant can be achieved.

Various fixation devices or tissue anchors, delivery devices, and methods are described for delivering and securing an implant within the body of the patient. The implants, fixation devices, delivery devices, and procedures described herein may be used in a female patient or a male patient.

An implant according to an embodiment of the invention can be implanted, for example, through a vaginal incision, in a retro-pubic direction (behind the pubic bone), or in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or an anterior vaginal incision. In some embodiments, a procedure may include an exterior incision.

Figure 1:
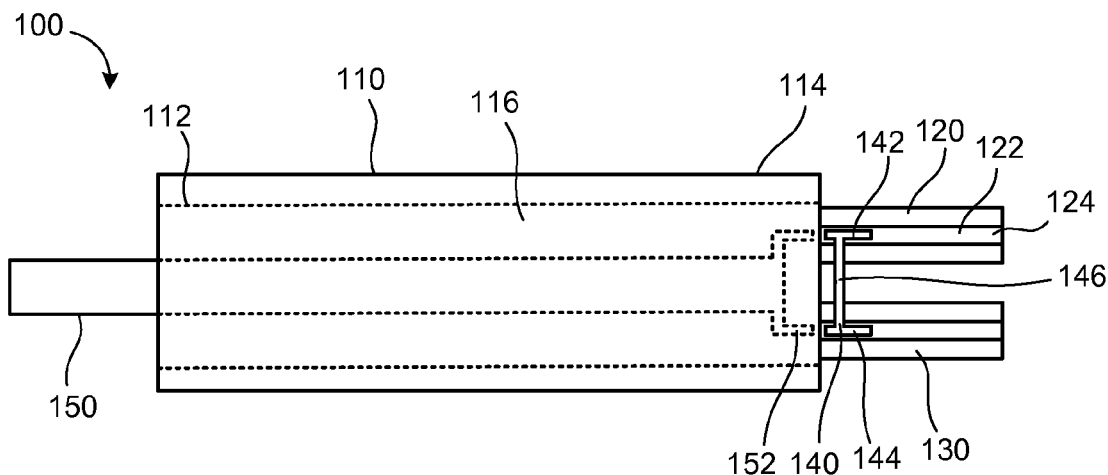
FIG. 1 is a schematic illustration of an apparatus according to an embodiment of the invention.

FIG. 1 is a schematic illustration of an apparatus or medical device 100 according to an embodiment of the invention. The apparatus or medical device 100 includes an elongate member 110, a first needle 120, a second needle 130, and a tissue anchor (or fixation device) 140. The illustrated embodiment also includes a pusher 150.

The apparatus 100 is configured to be inserted into a body of a patient such that at least a portion of the apparatus 100 is disposed within the body of the patient. As will be discussed in more detail below, the apparatus is configured to be placed adjacent a desired coupling or fixation location within the body.

The elongate member 110 includes a first end portion 112 and a second end portion 114. The elongate member 110 defines a lumen 116 (shown in dashed lines in FIG. 1). In some embodiments, the lumen 116 extends from the first end portion 112 to the second end portion 114. In some embodiments, the elongate member 110 defines an opening at the first end portion 112 and an opening at the second end portion 114 and the lumen 116 extends between the opening at the first end portion 112 and the opening at the second end portion 114. In other embodiments, the lumen only extends through a portion of the length of the elongate member 110. The lumen 116 is configured to receive and house various components of the apparatus 100 as will be described in detail below.

The first needle 120 and the second needle 130 are structurally and functionally similar. Accordingly, only the first needle 120 is described in detail.

The first needle 120 is coupled to and extends from the elongate member 110. In some embodiments, the first needle 120 extends from an end portion (such as end portion 114) of the elongate member 110. The first needle 120 is configured to be inserted into a bodily portion of a patient. For example, in some embodiments, the first needle 120 is configured to extend into bodily tissue of the patient. In some embodiments, the first needle 120 includes a sharp end portion that is configured to pierce bodily tissue.

In the illustrated embodiment, the first needle 120 includes or defines a lumen 124. The lumen 124 is configured to receive at least a portion of a tissue anchor 140. For example, in some embodiments, the lumen 124 is configured to receive or house a first arm portion or first side portion 142 of the tissue anchor 140. As will be described in more detail below, in some embodiments, the lumen 124 is configured receive or house at least a portion of the tissue anchor 140 such that the at least a portion of the tissue anchor 140 may move to various locations within the lumen 124 of the first needle. For example, in some embodiments, the lumen 124 is configured to receive or house at least a portion of the tissue anchor 140 such that the at least a portion of the tissue anchor 140 may move from a first location within the lumen 124, to a second location within the lumen 124, and to a third location within the lumen 124.

In some embodiments, the lumen 124 is configured to house the tissue anchor 140 such that the tissue anchor 140 may move to any number of locations within the lumen 124.

In some embodiments, the lumen 124 is configured to slideably receive or house the tissue anchor 140. In such embodiments, the portion of the tissue anchor 140 disposed within the lumen 124 is configured to slide within the lumen 124 to various locations within the lumen 124. In some embodiments, the tissue anchor 140 is configured to slide within the lumen 124 from a location within the lumen 124 to a location outside of the lumen 124. For example, when an end portion of the first needle 120 is disposed within bodily tissue of a patient, the portion of the tissue anchor 140 may be configured to move from a location within the lumen 124 to a location outside of the lumen 124 and within the bodily tissue of the patient.

In some embodiments, the lumen 124 is configured to house or receive an anchor portion of the tissue anchor 140. For example, in some embodiments, the tissue anchor 140 may include an anchor portion (such as an extension member, a barb, or a projection) that is configured to help anchor the tissue anchor 140 into bodily tissue of the patient. In some embodiments, the lumen 124 is configured to house or receive the anchor portion of the tissue anchor 140 such that the anchor portion of the tissue anchor 140 may move or slide to various locations within the lumen 124.

In some embodiments, the lumen 124 extends from one end portion of the first needle 120 to another end portion of the needle 120. For example, in some embodiments, the first needle 120 defines an opening at a first end portion of the first needle 120 and an opening at a second end portion of the first needle 120 and the lumen 124 extends between the openings. In other embodiments, the lumen 124 extends only along a portion of the length of the first needle 120.

In some embodiments, the first needle 120 defines a slot or elongated slot 122 defined by the sidewall of the first needle 120. In some embodiments, the slot or elongated slot 122 has a consistent width along the length of the slot 122. In such embodiments, the size or width of the slot 122 is such that the portion of the tissue anchor 140 disposed within the lumen 124 of the first needle 120 may not exit or be removed from the lumen 124 through the slot 122.

In other embodiments, the slot 122 has a first portion that defines a first width and a second portion that defines a second width. In such embodiments, the size or width of the slot 122 may be configured to retain or prevent the portion of the tissue anchor 140 disposed within the lumen 124 from leaving or exiting the lumen 124 along the first portion of the channel and may be wide enough to allow the portion of the tissue anchor 140 to be removed or separated from the first needle 120 along the second portion of the opening 124.

The tissue anchor or fixation device 140 is configured to be placed within a body of a patient and to be fixedly coupled to a portion of the body of the patient. For example, in some embodiments, the tissue anchor 140 is configured to engage a bodily implant and be coupled to body tissue within the body of the patient to fixedly couple the implant to the body tissue. In other embodiments, the tissue anchor 140 is configured to be coupled to body tissue and to a suture or a plurality of sutures that extend to and support a bodily implant.

In some embodiments, the tissue anchor or fixation device 140 includes a first arm portion 142, a second arm portion 144, and a base portion 146 disposed between the first arm portion 142 and the second arm portion 144. In some embodiments, the first arm portion 142 is configured to be disposed within the lumen 124 defined by the first needle 120. The second arm portion 144 is configured to be disposed within a lumen defined by the second needle 130. In some embodiments, the arm portions 142 and 144 are slideably disposed within the lumens defined by the needles 120 and 130.

The base portion 146 extends between the first arm portion 142 and the second arm portion 144. In some embodiments, the base portion 146 includes a first end portion coupled to the first arm portion 142 and a second end portion coupled to the second arm portion 144. For example, the base portion 146 may be coupled to the arm portions 142 and 144 via heat welding, an adhesive, or any other type of coupling. In some embodiments, the base portion 146 is unitarily formed with the first arm portion 142 and the second arm portion 144.

As will be discussed in more detail below, in some embodiments, the first arm portion 142 is sized such that it may be disposed within the lumen 124 of the first needle 120 and that it may not exit the lumen 124 through the opening or slot 124 of the first needle 120. Rather the first arm portion 142 must travel to the end of the needle to exit the lumen 124 via an opening defined by the first needle 120. In other embodiments, the slot 122 includes a narrow portion and a wide portion. In such embodiments, the first arm portion 142 may exit the lumen 124 through the wide portion of the slot 122. The second arm portion 144 may be functionally and structurally similar to the first arm portion 142.

In some embodiments, the base portion 146 is sized such that it may extend though the slot 122 defined by the sidewall of the first needle 120 and through the slot of the second needle 130.

In some embodiments, the first arm portion 142 and the second arm portion 144 include an anchor member (such as a projection, a barb, or an extension member). In some embodiments, the first arm portion 142 and the second arm portion 144 include tissue piercing portions. For example, in some embodiments, a distal end portion of the first arm portion 142 and a distal end portion of the second arm portion 144 include a sharp point or portion that is configured to pierce bodily tissue as the tissue anchor 140 is inserted into bodily tissue.

The tissue anchor 140 may be made of any suitable biocompatible material. For example, in some embodiments, the tissue anchor 140 is formed of a polymer or plastic material. In other embodiments, the tissue anchor 140 is formed of a metal. In some embodiments, the base portion 146 of the tissue anchor 140 is formed of a flexible material.

In the illustrated embodiment, the apparatus 100 includes a pusher 150. The pusher 150 is configured to be disposed within the lumen 116 defined by the elongate member 110. For example, in some embodiments, the pusher 150 is configured to be disposed within the lumen 116 such that a portion of the pusher 150 is disposed within the lumen 116 and a portion of the pusher 150 is disposed outside of the lumen 116.

The pusher 150 is configured to move from a first location to a second location with respect to the elongate member 110. For example, in some embodiments, the pusher 150 is configured to move from a first location within the lumen 116 to a second location within the lumen 116 different than the first location.

In the illustrated embodiment, the pusher 150 includes a contact portion 152 that is configured to contact the tissue anchor 140 while the tissue anchor 140 is at least partially disposed within the lumens defined by the first needle 120 and the second needle 130. For example, in some embodiments, when the pusher 150 is at its first position within the lumen 116 the pusher 150 does not contact the tissue anchor 140. As the pusher 150 is moved from its first position to its second position, the pusher 150 contacts the tissue anchor 140 and moves the tissue anchor 140 within the lumens defined by the first needle 120 and the second needle 130. In some embodiments, the pusher 150 is configured to expel or push the tissue anchor 140 to a location outside of the lumens defined by the first needle 120 and the second needle 130 when the pusher 150 is in its second position.

In some embodiments, the lumens defined by the first needle 120 and the second needle 130 are configured to house or receive a plurality of tissue anchors. For example, in some embodiments, the lumens are configured to house or receive two tissue anchors. In some embodiments, the tissue anchors may be disposed serially or end to end within the lumens. In such embodiments, the pusher 150 may be configured to contact and move one of the tissue anchors, which may in turn be configured to contact and move the other of the tissue anchors.

In use, a tissue anchor 140 may be disposed within the lumens defined by the first needle 120 and the second needle 130 such that the tissue anchor 140 is retained within the lumens. Specifically, the anchor 140 is disposed within the lumens such that the first arm portion 142 is disposed within the lumen 124 of the first needle, the second arm portion 144 is disposed within the lumen of the second needle 130, and the base portion 146 extends from the lumens between the first arm portion 142 and the second arm portion 144.

The apparatus 100 may then be inserted into a body of a patient. For example, in some implementations, the apparatus 100 may be inserted into a body of a patient through a vaginal incision. The first needle 120 and the second needle 130 may be disposed adjacent to the bodily tissue into which the tissue anchor 140 is to be inserted. In some embodiments, a bodily implant, such as a mesh type bodily implant, may be disposed adjacent the bodily tissue and pierced by the needles 120 and 130.

The pusher 150 may then be moved with respect to the elongate member 110 within the lumen 116 defined by the elongate member 110. For example, the pusher may be moved from a first position to a second position. As the pusher is moved from its first position or location within the lumen 116 to its second position or location within the lumen 116, the pusher 140 contacts and moves the tissue anchor 140 from a location within the lumens of the needles 120 and 130 to a location outside of the lumens and into the bodily tissue. Accordingly, the tissue anchor 140 is coupled or fixed within the bodily tissue.

In some embodiments, the medical device includes a second tissue anchor. In such embodiments, the medical device may then be moved to another location within the body (and disposed adjacent different or another portion of bodily tissue). The second tissue anchor may then be inserted to such portion of bodily tissue.

Figure 2:
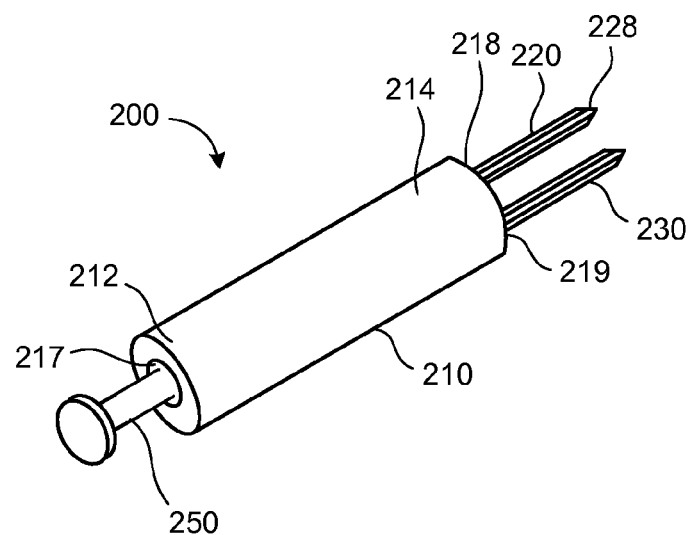
FIG. 2 is a perspective view an apparatus according to an embodiment of the invention.
Figure 3:
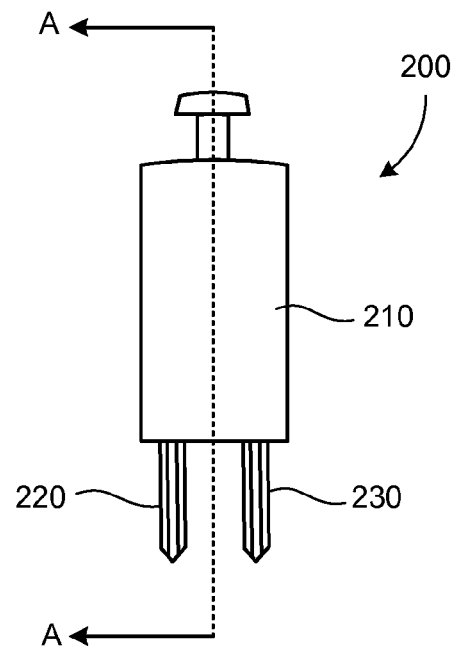
FIG. 3 is a side view of the apparatus of FIG. 2.
Figure 4:
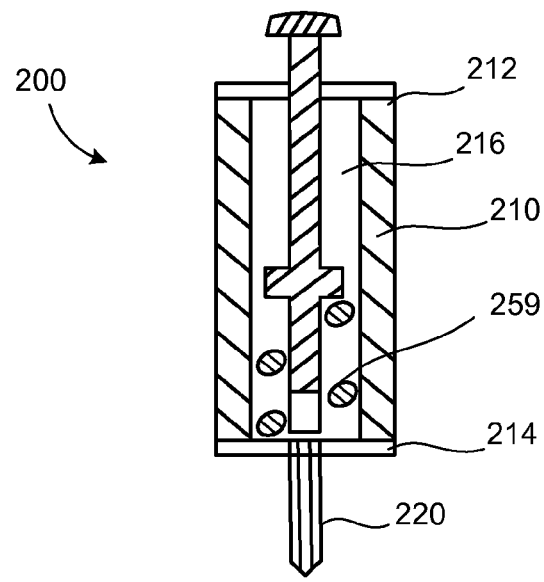
FIG. 4 is a cross-sectional view of the apparatus of FIG. 2 taken along line A-A of FIG. 3.
Figure 5:
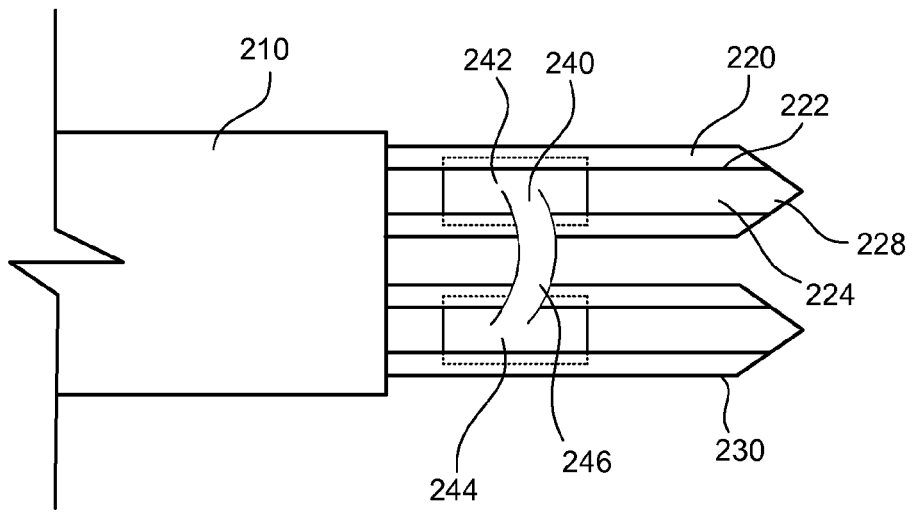
FIG. 5 is a side view of a distal end portion of the apparatus of FIG. 2.

FIG. 2 is a perspective view of an apparatus or medical device 200 according to an embodiment of the invention. FIG. 3 is a side view of the apparatus 200. FIG. 4 is a cross-sectional view of the apparatus 200 taken along line A-A of FIG. 3. FIG. 5 is a side view of an end portion of the apparatus 200 and a tissue anchor 240.

The apparatus or medical device 200 includes an elongate member 210, a first needle 220, a second needle 230, and a tissue anchor (or fixation device) 240. The illustrated embodiment also includes a pusher 250.

The apparatus 200 is configured to be inserted into a body of a patient such that at least a portion of the apparatus 200 is disposed within the body of the patient. As will be discussed in more detail below, the apparatus is configured to be placed adjacent a desired coupling or fixation location within the body.

The elongate member 210 is a tubular or cylindrical member and includes a first end portion 212 and a second end portion 214. The elongate member 210 defines a lumen 216. In the illustrated embodiment, the lumen 216 extends from the first end portion 212 to the second end portion 214. In the illustrated embodiment, the elongate member 210 defines an opening 217 at the first end portion 212 and openings 218 and 219 at the second end portion 214 and the lumen 216 extends between the opening 217 at the first end portion 212 and the openings 218 and 219 at the second end portion 214.

The first needle 220 and the second needle 230 are structurally and functionally similar. Accordingly, only the first needle 220 is described in detail.

Figure 6:
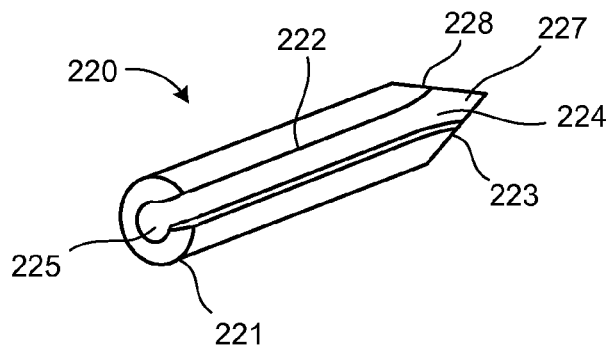
FIG. 6 is a perspective view of a needle member of the device of FIG. 2.

FIG. 6 is a perspective view of the first needle 220. The first needle 220 is coupled to and extends from the elongate member 210. The first needle 220 is configured to be inserted into a bodily portion of a patient. For example, in some embodiments, the first needle 220 is configured to extend into bodily tissue of the patient. The first needle 220 includes a sharp end portion 228 that is configured to pierce bodily tissue.

In the illustrated embodiment, the first needle 220 includes or defines a lumen 224. The lumen 224 is configured to receive at least a portion of a tissue anchor 240. For example, in some embodiments, the lumen 224 is configured to receive or house a first arm portion or first side portion 242 of the tissue anchor 240. As will be described in more detail below, the lumen 224 is configured receive or house at least a portion of the tissue anchor 240 such that the at least a portion of the tissue anchor 240 may move to various locations within the lumen 224 of the first needle 220. For example, in some embodiments, the lumen 224 is configured to receive or house at least a portion of the tissue anchor 240 such that the at least a portion of the tissue anchor 240 may move from a first location within the lumen 224, to a second location within the lumen 224, and to a third location within the lumen 224. In some embodiments, the lumen 224 is configured to house the tissue anchor 240 such that the tissue anchor 240 may move to any number of locations within the lumen 224.

The lumen 224 is configured to slideably receive or house the tissue anchor 240. The portion of the tissue anchor 240 disposed within the lumen 224 is configured to slide within the lumen 224 to various locations within the lumen 224. In some embodiments, the tissue anchor 240 is configured to slide within the lumen 224 from a location within the lumen 224 to a location outside of the lumen 224. For example, when an end portion of the first needle 220 is disposed within bodily tissue of a patient, the portion of the tissue anchor 240 may be configured to move from a location within the lumen 224 to a location outside of the lumen 124 and within the bodily tissue of the patient.

In some embodiments, the lumen 224 is configured to house or receive an anchor portion of the tissue anchor 240. For example, in some embodiments, the tissue anchor may include an anchor portion (such as an extension member, a barb, or a projection) that is configured to help anchor the tissue anchor into bodily tissue of the patient. In some embodiments, the lumen 224 is configured to house or receive the anchor portion of the tissue anchor such that the anchor portion of the tissue anchor may move or slide to various locations within the lumen 224.

In the illustrated embodiment, the lumen 224 extends from one end portion 221 of the first needle 220 to another end portion 223 of the needle 220. The first needle 120 defines an opening 225 at the first end portion 221 of the first needle 220 and an opening 227 at a second end portion 223 of the first needle 220 and the lumen 224 extends between the openings 225 and 227. In other embodiments, the lumen extends only along a portion of the length of the first needle.

The first needle 220 is coupled to the elongate member 210 such that the opening 225 communicates with the lumen 216 defined by the elongate member 210. Specifically, the opening 225 is in fluid communication with the lumen 216 via the opening 218 defined by the distal end portion 214 of the elongate member 210. Accordingly, the pusher 250, such as the contact portion 252 of the pusher 250 may extend from the lumen 216 defined by the elongate member 210 into the lumen 224 defined by the first needle 220.

In some embodiments, the first needle 220 defines a slot or elongated opening 222 defined by the sidewall of the first needle 220. In the illustrated embodiment, the slot or elongated opening 222 has a consistent width along the length of the slot 222. The portion of the tissue anchor 240 disposed within the lumen 224 may move within the lumen 224 and exit the lumen through the opening 227 defined by the end portion 223 of the first needle 220. The size or width of the slot 222 is such that the portion of the tissue anchor 240 disposed within the lumen 224 of the first needle 220 may not exit or be removed from the lumen 224 through the slot 222.

Figure 7:
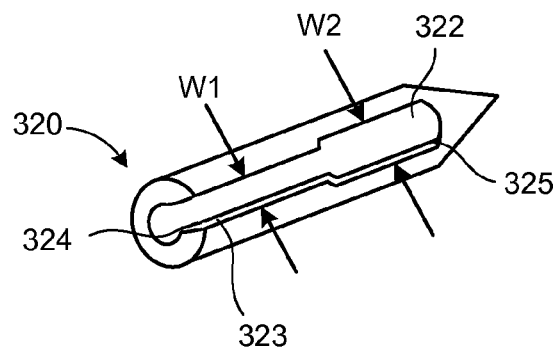
FIG. 7 is a perspective view of another needle member.

As illustrated in FIG. 7, in other embodiments, a needle 320 includes a slot or elongated opening 322. The slot 322 has a first portion 323 that defines a first width W1 and a second portion 325 that defines a second width W2. The size or width of the slot 322 may be configured to retain or prevent the portion of the tissue anchor disposed within the lumen 324 from leaving or exiting the lumen 324 along the first portion of the slot and may be wide enough to allow the portion of the tissue anchor to be removed or separated from the first needle along the second portion 325 of the slot 322.

Figure 8:
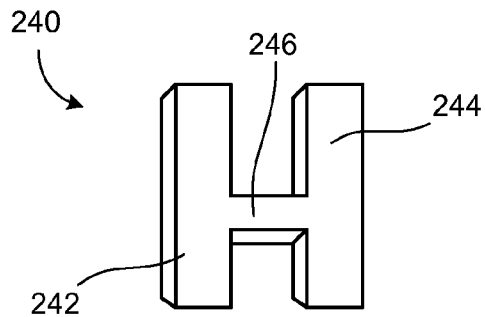
FIGS. 8-14 are perspective views of tissue anchors.

FIG. 8 is a perspective view of a tissue anchor 240. The tissue anchor or fixation device 240 is configured to be placed within a body of a patient and to be fixedly coupled to a portion of the body of the patient. For example, in some embodiments, the tissue anchor 240 is configured to engage a bodily implant and be coupled to body tissue within the body of the patient to fixedly couple the implant to the body tissue. In other embodiments, the tissue anchor 240 is configured to be coupled to body tissue and to a suture or a plurality of sutures that extend to and support a bodily implant.

The tissue anchor or fixation device 240 includes a first arm portion 242, a second arm portion 244, and a base portion 246 disposed between the first arm portion 242 and the second arm portion 244. The first arm portion 242 is configured to be disposed within the lumen 224 defined by the first needle 220. The second arm portion 244 is configured to be disposed within a lumen defined by the second needle 230. In some embodiments, the arm portions 242 and 244 are slideably disposed within the lumens defined by the needles 220 and 230.

The base portion 246 extends between the first arm portion 242 and the second arm portion 244. In some embodiments, the base portion 246 includes a first end portion coupled to the first arm portion 242 and a second end portion coupled to the second arm portion 244. For example, the base portion 246 may be coupled to the arm portions 242 and 244 via heat welding, an adhesive, or any other type of coupling. In some embodiments, the base portion 246 is unitarily formed with the first arm portion 242 and the second arm portion 244.

The first arm portion 242 is sized such that it may be disposed within the lumen 224 of the first needle 220 and that it may not exit the lumen 224 through the opening or slot 224 of the first needle 220. Rather the first arm portion 242 must travel to the end of the needle to exit the lumen 224 via the opening 228 defined by the first needle 220.

In other embodiments (such as illustrated in FIG. 7), the slot 322 includes a narrow portion 323 and a wide portion 325. In such embodiments, the first arm portion 242 may not exit the lumen 324 through the narrow portion 323 of the slot 322 but may exit the lumen 324 through the wide portion 325 of the slot 322.

In some embodiments, the second arm portion 244 may be functionally and structurally similar to the first arm portion 242. The second arm portion 244 is configured to be movably disposed within a lumen defined by the second needle 230.

As best illustrated in FIG. 5, the base portion 246 of the tissue anchor 240 is sized such that it may extend though the slot 222 defined by the sidewall of the first needle 220 and through the slot of the second needle 130.

In some embodiments, the first arm portion 242 and the second arm portion 244 include an anchor member (such as a projection, a barb, or an extension member). In some embodiments, the first arm portion 242 and the second arm portion 244 include tissue piercing portions. For example, in some embodiments, a distal end portion of the first arm portion 242 and a distal end portion of the second arm portion 244 include a sharp point or portion that is configured to pierce bodily tissue as the tissue anchor 240 is inserted into bodily tissue.

The tissue anchor 240 may be made of any suitable biocompatible material. For example, in some embodiments, the tissue anchor 240 is formed of a polymer or plastic material. In other embodiments, the tissue anchor 240 is formed of a metal material. In some embodiments, the base portion 246 of the tissue anchor 240 is formed of a flexible material.

Figure 9:
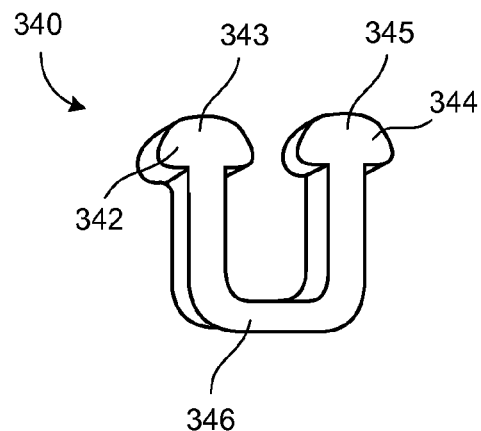

FIGS. 9-14 are perspective views of other tissue anchors. FIG. 9 is a perspective view of tissue anchor 340. The tissue anchor 340 includes a first arm portion 342, a second arm portion 344, and a base portion 346. The first arm portion 342 includes an anchor member 343 and the second arm portion 344 includes an anchor member 345. The anchor members 343 and 345 are configured to help retain the tissue anchor within bodily tissue of the patient.

Figure 10:
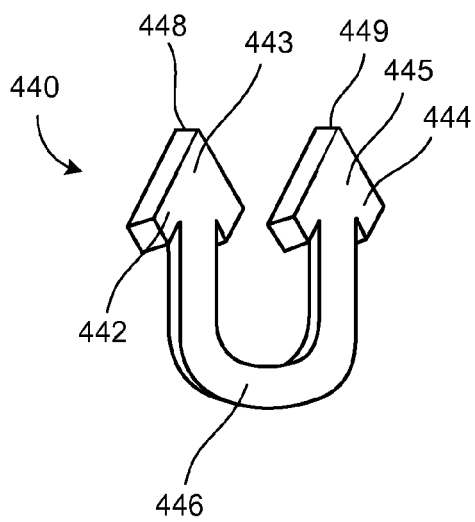

FIG. 10 is a perspective view of tissue anchor 440. The tissue anchor 440 includes a first arm portion 442, a second arm portion 444, and a base portion 446. The first arm portion 442 includes an anchor member 443 and the second arm portion 444 includes an anchor member 445. The anchor members 443 and 445 include are barbs or projections and are configured to help retain the tissue anchor within bodily tissue of the patient. In some embodiments, the arm portions 442 and 444 (including the anchor members 443 and 445) may be configured to fold or flex to allow portions of the tissue anchor 440 to fit within the lumens defined by the needle members. The arm portions 442 and 444 also each include tissue piercing portions 448 and 449, respectively, that are configured to pierce bodily tissue. The base portion 446 includes a curved portion.

Figure 11:
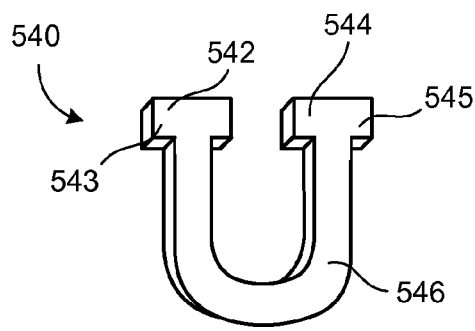

FIG. 11 is a perspective view of tissue anchor 540. The tissue anchor 540 includes a first arm portion 542, a second arm portion 544, and a base portion 546. The first arm portion 542 includes an anchor member 543 and the second arm portion 544 includes an anchor member 545. The anchor members 543 and 545 are configured to help retain the tissue anchor within bodily tissue of the patient. The base portion 546 includes a curved portion.

Figure 12:
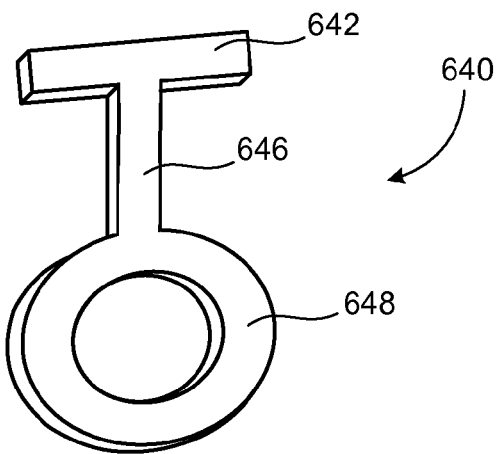

FIG. 12 is a perspective view of tissue anchor 640. The tissue anchor 640 includes an arm portion 642, a base portion 646, and a suture coupling portion 648. The tissue anchor 640 may be delivered to the body of the patient using a device that only includes a single needle member. Alternatively, only a single needle member (of a device that includes more than one needle member) is used to deliver the tissue anchor 640.

The arm portion 642 is configured to be slideably coupled within the lumen of a needle. The base portion 646 extends between the arm portion 642 and the suture coupling portion 648. The suture coupling portion 648 includes a ring portion. The suture coupling portion 648 is configured to be coupled to a suture or a plurality of sutures. For example, a suture or a plurality of sutures may be tied, looped through, or otherwise coupled to the suture coupling portion 648. In some embodiments, a plurality of sutures are threaded or looped through the suture coupling portion 648 and then tied or otherwise coupled to a bodily implant. Thus, the bodily implant may be supported or hung from the tissue anchor 640 via sutures coupled to the suture coupling portion 648.

Figure 13:
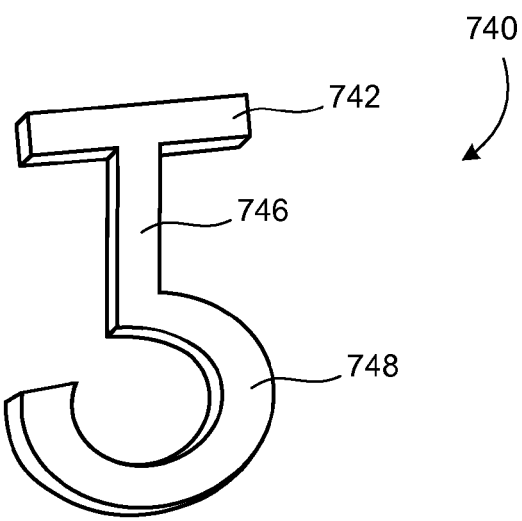
Figure 14:
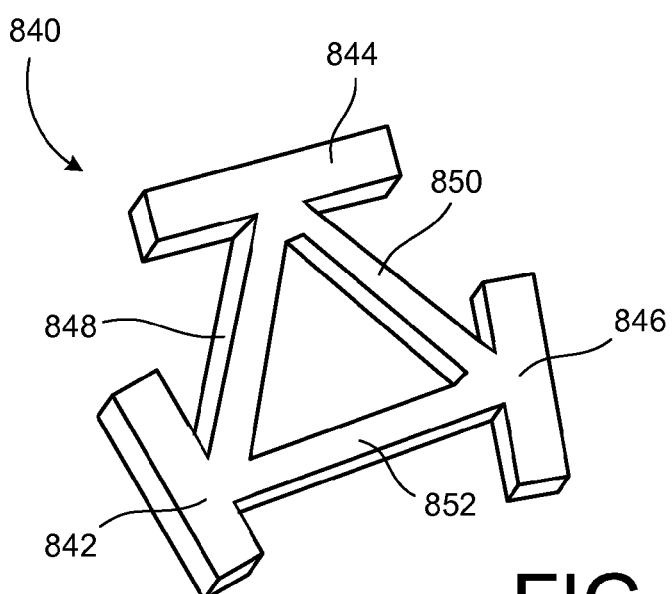

FIG. 13 is a perspective view of tissue anchor 740. The tissue anchor 740 includes an arm portion 742, a base portion 746, and a suture coupling portion 748. The tissue anchor 740 may be delivered to the body of the patient using a device that only includes a single needle member. Alternatively, only a single needle member (of a device that includes more than one needle member) is used to deliver the tissue anchor 740.

The arm portion 742 is configured to be slideably coupled within the lumen of a needle member. The base portion 746 extends between the arm portion 742 and the suture coupling portion 748. The suture coupling portion 748 includes a J-shaped portion. The suture coupling portion 748 is configured to be coupled to a suture or a plurality of sutures. For example, a suture or a plurality of sutures may be tied or otherwise coupled to the suture coupling portion 748. In some embodiments, a plurality of sutures are coupled to the suture coupling portion 748 and then tied or otherwise coupled to a bodily implant. Thus, the bodily implant may be supported or hung from the tissue anchor 740 via sutures coupled to the suture coupling portion 748.

FIG. 13 is a perspective view of tissue anchor 840. The tissue anchor 840 includes a first arm portion 842, a second arm portion 844, a third arm portion 846, a first base portion 848, a second base portion 850, and a third base portion 852. The tissue anchor 840 may be delivered to a body of a patient using a device that includes three needle members. The three arms 842, 844, and 846 are configured to be coupled to bodily tissue and provide support to the tissue anchor 840.

The first base portion 848 extends between the first arm portion 842 and the second arm portion 844. The second base portion 850 extends between the second arm portion 844 and the third arm portion 846. The third base portion 852 extends between the third arm portion 846 and the first arm portion 842. The base portions 848, 850, and 852 configured to be coupled to sutures to allow bodily implants to be suspended from the tissue anchor 840 via the sutures.

The apparatus 200 includes a pusher 250. The pusher 250 is configured to be disposed within the lumen 216 defined by the elongate member 210. For example, in some embodiments, the pusher 250 is configured to be disposed within the lumen 216 such that a portion of the pusher 250 is disposed within the lumen 216 and a portion of the pusher 250 is disposed outside of the lumen 216.

The pusher 250 is configured to move from a first location to a second location with respect to the elongate member 210. For example, in some embodiments, the pusher 250 is configured to move from a first location within the lumen 216 to a second location within the lumen 216 different than the first location.

In the illustrated embodiment, the pusher 250 includes a contact portion 252 that is configured to contact the tissue anchor 240 while the tissue anchor 240 is at least partially disposed within the lumens defined by the first needle 220 and the second needle 230. For example, in some embodiments, when the pusher 250 is at its first position within the lumen 216 the pusher 250 does not contact the tissue anchor 240. As the pusher 250 is moved from its first position to its second position, the pusher 250 contacts the tissue anchor 240 and moves the tissue anchor 240 within the lumens defined by the first needle 220 and the second needle 230. Specifically, a first portion of the contact portion 252 contacts the first arm portion 242 and a second portion of the contact portion 254 contacts the second arm portion 244. In some embodiments, the pusher 250 is configured to expel or push the tissue anchor 240 to a location outside of the lumens defined by the first needle 220 and the second needle 230 when the pusher 250 is in its second position.

In the illustrated embodiment, the pusher 250 is biased to one of its positions. For example, the pusher may be biased to its first portion (to be out of contact with the tissue anchor). As best illustrated in FIG. 4, the pusher 250 includes a projection portion 258. The projection portion 258 extends or projects from the pusher 250. The projection portion 258 is configured to contact a biasing member (such as a spring) 259 to bias the pusher 250 to its first position. In the illustrated embodiment, the biasing member 259 is disposed within the lumen 216 between an end portion of the elongate member and the projection portion 258 of the pusher 250.

In some embodiments, the lumens defined by the first needle 220 and the second needle 230 are configured to house or receive a plurality of tissue anchors. For example, in some embodiments, the lumens are configured to house or receive two tissue anchors. In some embodiments, the tissue anchors may be disposed serially or end to end within the lumens. In such embodiments, the pusher 250 may be configured to contact and move one of the tissue anchors, which may in turn be configured to contact and move the other of the tissue anchors.

In use, a tissue anchor 240 may be disposed within the lumens defined by the first needle 220 and the second needle 230 such that the tissue anchor 240 is retained within the lumens. Specifically, the anchor 240 is disposed within the lumens such that the first arm portion 242 is disposed within the lumen 224 of the first needle, the second arm portion 244 is disposed within the lumen of the second needle 230, and the base portion 246 extends from the lumens between the first arm portion 242 and the second arm portion 244.

Figure 15:
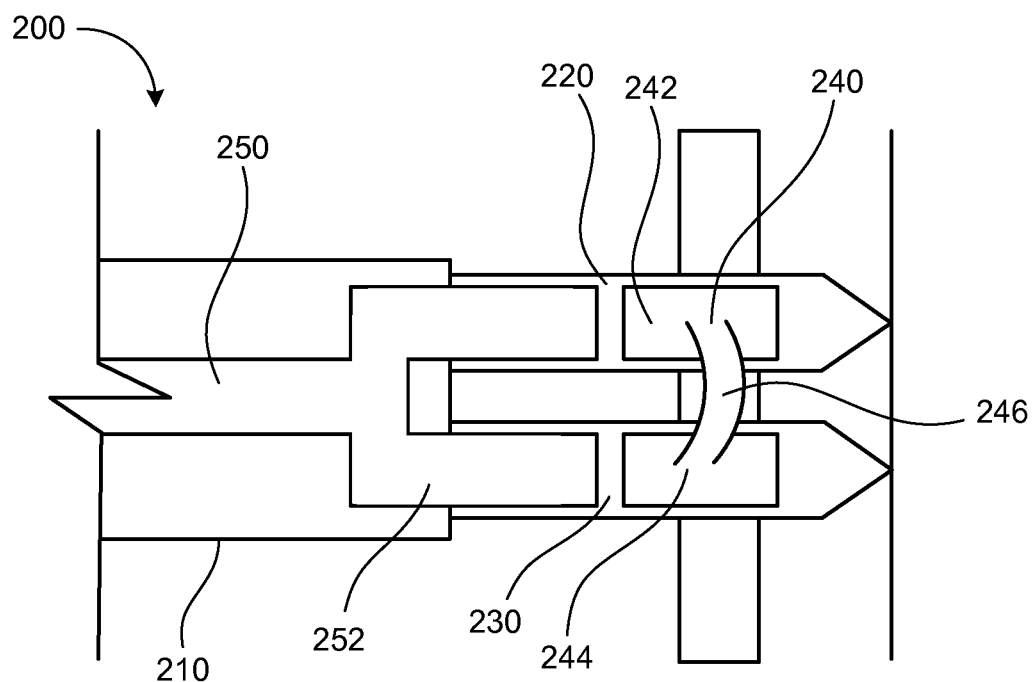
FIG. 15 is a schematic illustration of an end portion of the apparatus of FIG. 2.

FIG. 15 schematically illustrates a tissue anchor being inserted into bodily tissue BT of a patient. The apparatus 200 is inserted into a body of a patient. For example, in some implementations, the apparatus 200 may be inserted into a body of a patient through a vaginal incision. The first needle 220 and the second needle 230 may be disposed adjacent to the bodily tissue into which the tissue anchor 240 is to be inserted. In some embodiments, a bodily implant I, such as a mesh type bodily implant, may be disposed adjacent the bodily tissue and pierced by the needles 220 and 230 (as illustrated in FIG. 15). In some embodiments, the distance between the needles 220 and 230 is at least as large or wide as the filament members that form the mesh implant I.

Figure 16:
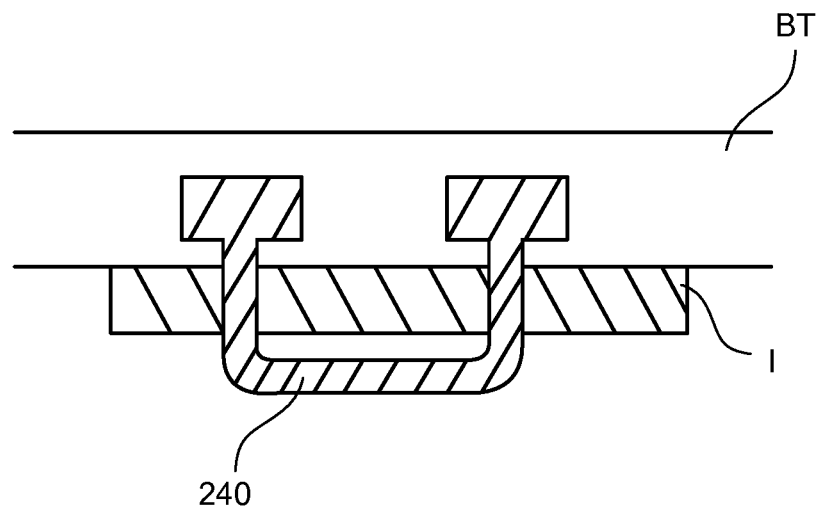
FIG. 16 is a schematic cross-sectional view of a tissue anchor disposed within bodily tissue.

The pusher 250 may then be moved with respect to the elongate member 210 within the lumen 216 defined by the elongate member 110. For example, the pusher may be moved from a first position to a second position. As the pusher is moved from its first position or location within the lumen 116 to its second position or location within the lumen 216, the pusher 240 contacts and moves the tissue anchor 240 from a location within the lumens FIG. 16 is schematic cross-sectional view of the tissue anchor 240 extending through the bodily implant I and anchored in bodily tissue BT to support or anchor the bodily implant I to the bodily tissue BT.

In some embodiments, the medical device includes a second tissue anchor. In such embodiments, the medical device may then be moved to another location within the body (and disposed adjacent different or another portion of bodily tissue). The second tissue anchor may then be inserted to such portion of bodily tissue.

Figure 17:
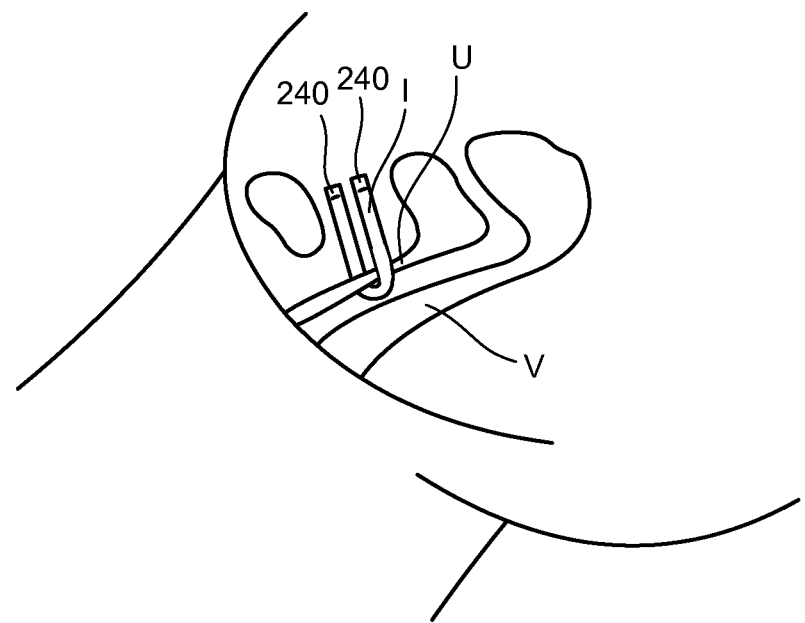
FIGS. 17 and 18 are schematic illustrations of implants disposed within a body of a patient.

FIG. 17 schematically illustrates an implant I disposed within a pelvic region of a patient. The end portions of the implant I are coupled to bodily tissue via tissue anchors 240. The implant I extends beneath the urethra U of the patient and is configured to provide support to the urethra U. In some embodiments, the implant I may be inserted into the body of the patient (using an apparatus as described above) via an incision in the wall of the vagina V.

Figure 18:
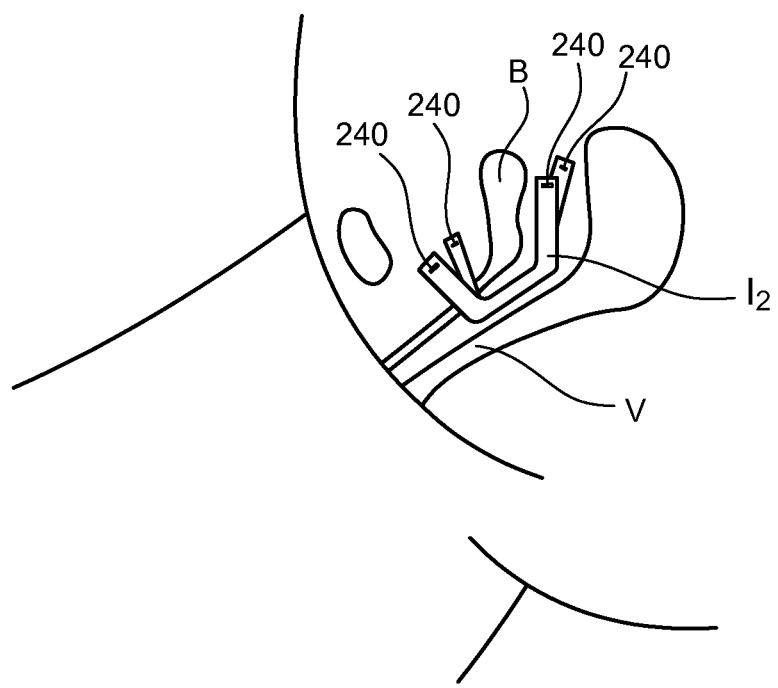

FIG. 18 schematically illustrates another implant 12 disposed within a pelvic region of a patient. The end portions or arms of the implant 12 are coupled to bodily tissue via tissue anchors 240. The implant 12 is extends beneath the bladder B of the patient and is configured to provide support to the bladder B. In some embodiments, the implant 12 may be inserted into the body of the patient (using an apparatus as described above) via an incision in the wall of the vagina V.

Figure 19:
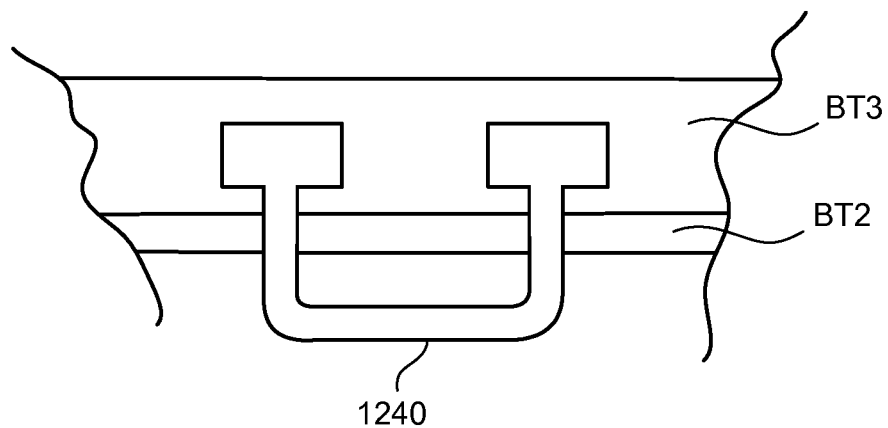
FIGS. 19-20 are schematic illustrations of tissue anchors disposed within bodily tissue.

In some embodiments, the device 200 may be used to couple a first portion of bodily tissue to a second portion of bodily tissue. FIG. 19 schematically illustrates a tissue anchor 1240 disposed within bodily tissue to couple a first portion of bodily tissue BT2 to a second portion of bodily tissue BT3.

Figure 20:
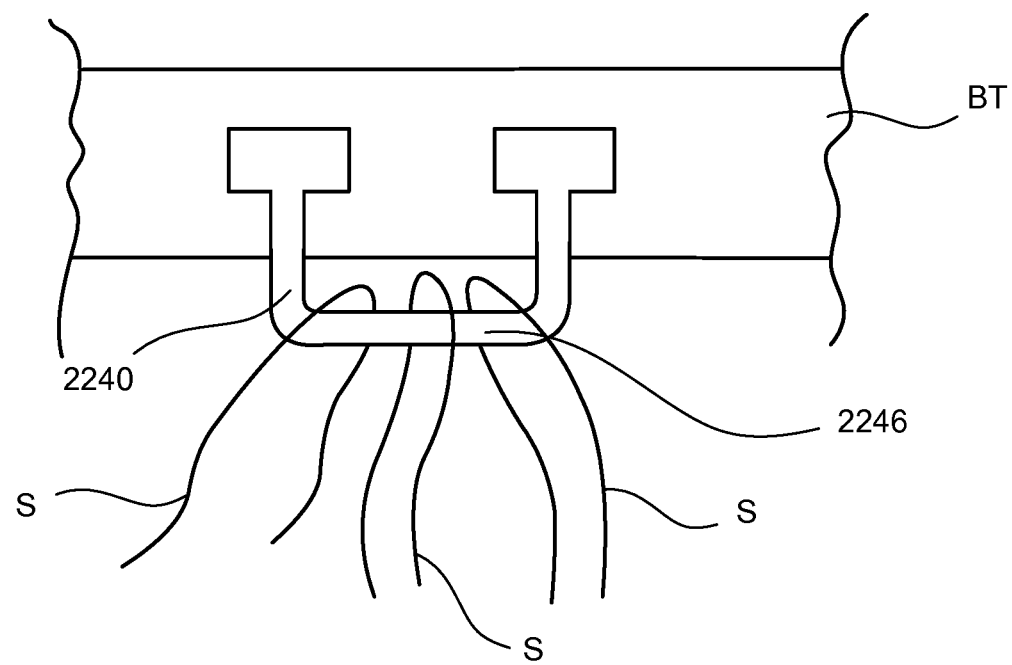

In some embodiments, the device 200 may be used to couple a tissue anchor 2240 to bodily tissue. Sutures or other extension members may then be coupled to the tissue anchor to provide support to a bodily implant. For example, sutures may be coupled at one end of the suture to the tissue anchor and at another end to the bodily implant. In other embodiments, as illustrated in FIG. 20, sutures S, may be looped through around a portion of the tissue anchor 2240 (such as the base portion 2246 between the base portion 2246 and the bodily tissue BT). The sutures S may then be coupled to a bodily implant at various locations or may be coupled to different bodily implants to help support the implants within a body of a patient. In the illustrated embodiment, three sutures S are coupled to the tissue anchor 2240. However, any number of sutures may be coupled to the tissue anchor 2240.

Figure 21:
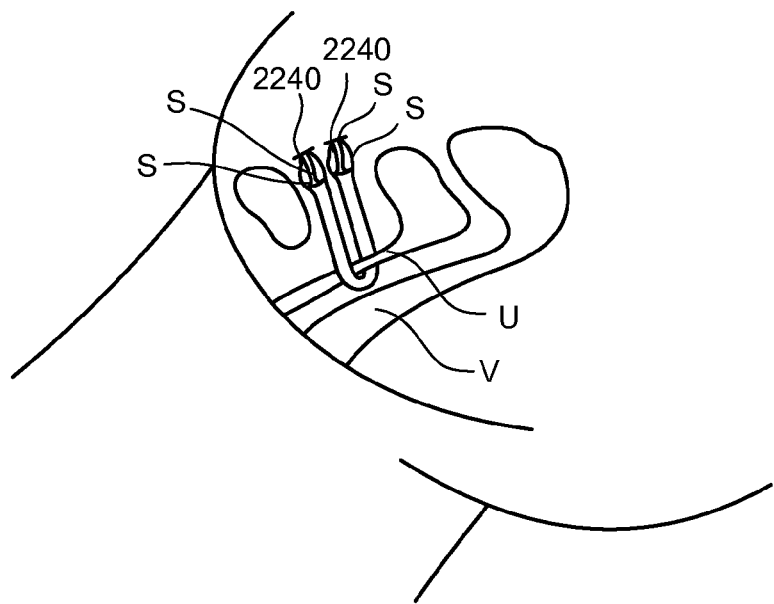
FIG. 21 is a schematic illustration of an implant disposed within a body of a patient.

FIG. 21 schematically illustrates an implant I disposed within a pelvic region of a patient. The end portions of the implant I are coupled to bodily tissue via sutures S which are coupled to tissue anchors 2240. The implant I extends beneath the urethra U of the patient and is configured to provide support to the urethra U. In some embodiments, the implant I may be inserted into the body of the patient (using an apparatus as described above) via an incision in the wall of the vagina V.

Figure 22:
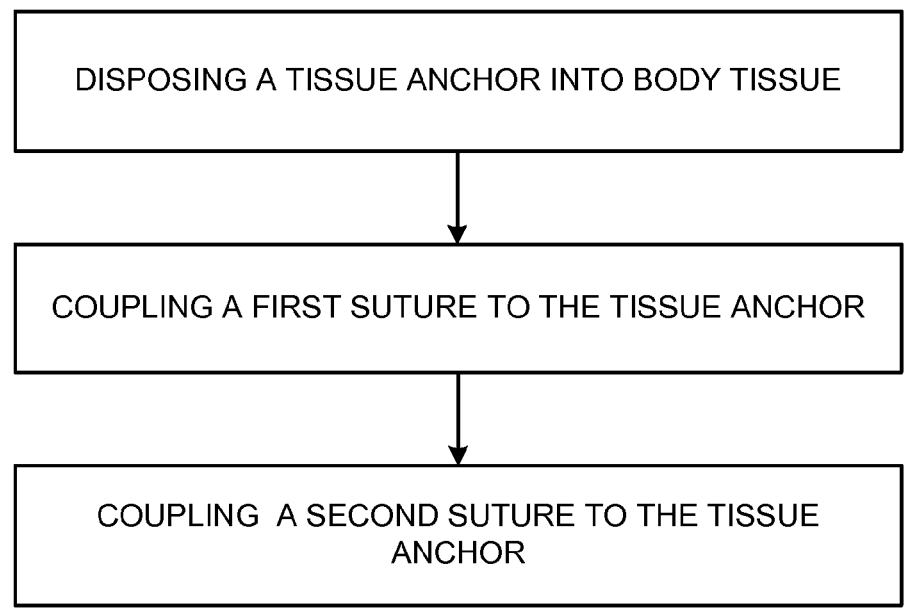
FIG. 22 is a flow chart of a method of placing an implant within a body of a patient.

FIG. 22 is a flow chart for a method 1500 of coupling a bodily implant within a body of a patient. At 1510, the tissue anchor is disposed within bodily tissue of a patient. In some embodiments, the anchor is placed with a device such as device 200. In some embodiments, the anchor is inserted into the body of the patient though a vaginal incision. In some embodiments, an arm portion or member of the anchor is disposed within bodily tissue. In some embodiments, the arm portion or member is inserted into the bodily tissue via a pusher of the medical or implantation device.

At 1520, a first suture is coupled to the tissue anchor. The suture may be tied or looped through a portion of the anchor to couple to the suture to the bodily implant.

At 1530, a second suture is coupled to the tissue anchor. The suture may be tied or looped through a portion of the anchor to couple the suture to the bodily implant.

In some embodiments, the sutures are also coupled to bodily implants. In some embodiments, all of the sutures are coupled to the same implant to help support the implant within the body of the patient. In other embodiments, the sutures are coupled to different implants to help support the implants within the body of the patient.

In some embodiments, a medical device includes a tissue anchor, an elongate member, a first needle and a second needle. The tissue anchor is configured to be disposed within bodily tissue and has a first arm portion, a second arm portion, and a base portion extending between the first arm portion and the second arm portion. The first needle extends from the elongate member. The first needle defines a lumen configured to receive at least a portion of the first arm portion of the tissue anchor. The second needle extends from the elongate member. The second needle defines a lumen configured to receive at least a portion of the second arm portion of the tissue anchor.

In some embodiments, the medical device includes a pusher. The pusher is configured to contact and move the tissue anchor such that the first arm portion of the tissue anchor moves from a first location within the lumen defined by the first needle to a second location within the lumen defined by the needle and the second arm portion of the tissue anchor moves from a first location within the lumen defined by the second needle to a second location within the lumen defined by the second needle.

In some embodiments, the pusher includes an elongate portion and a contact portion, the elongate portion being disposed within a lumen defined by the elongate member. In some embodiments, the pusher includes an elongate portion and a contact portion. The elongate portion is disposed within a lumen defined by the elongate member. The contact portion has a first portion configured to contact the first portion of the tissue anchor and a second portion configured to contact the second portion of the tissue anchor. In some embodiments, the pusher is slideably coupled to the elongate member. In some embodiments, the pusher is slideably coupled within a lumen defined by the elongate member.

In some embodiments, the medical device includes a housing configured to house a plurality of tissue anchors. In some embodiments, the medical device includes a housing defining a cavity. The cavity is configured to house a plurality of tissue. The cavity is operatively coupled to the groove of the first needle and the groove of the second needle.

In some embodiments, the medical device is configured to be inserted into a body of a patient.

In some embodiments, the base portion is a first base portion. The tissue anchor includes a third arm portion, a second base portion, and a third base portion. The second base portion extends between the second arm portion and the third arm portion. The third base portion extends between the third arm portion and the first arm portion. In some embodiments, the first arm portion includes an anchor member and the second arm portion includes an anchor member. The lumen of the first needle is configured to receive the anchor member of the first arm portion. The lumen of the second needle is configured to receive the anchor member of the second arm portion.

In some embodiments, a method includes inserting a medical device into a body of a patient, the medical device including an elongate member, a first needle extending from the elongate member, a second needle extending from the elongate member, and a pusher disposed within a lumen defined by the elongate member; and moving a tissue anchor into bodily tissue of the patient.

In some embodiments, the inserting includes placing the first needle and the second needle into bodily tissue of the patient. In some embodiments, the inserting includes disposing the medical device adjacent bodily tissue such that a bodily implant is disposed between the medical device and the bodily tissue. In some embodiments, the moving includes moving the pusher within the lumen defined by the elongate member. In some embodiments, the moving includes using the pusher to contact and move a first portion of the tissue anchor from a location within a lumen defined by the first needle to a location outside of the lumen defined by the first needle.

In some embodiments, a method includes disposing a tissue anchor into bodily tissue of a patient, the tissue anchor having a first arm portion, a second arm portion, and a base portion disposed between the first arm portion and the second arm portion; coupling a first suture to the tissue anchor; and coupling a second suture to the tissue anchor.

In some embodiments, the disposing includes disposing the tissue anchor into bodily tissue of the patient such that at least a portion of the first arm is disposed in bodily tissue and at least a portion of the second arm is disposed in bodily tissue.

In some embodiments, the disposing includes inserting a medical device into a body of the patient such that a first needle and a second needle of the medical device are disposed within the bodily tissue, and moving a pusher of the medical device such that the pusher contacts the tissue anchor to expel a the first arm portion of the tissue anchor from a lumen defined by the first needle and the second arm portion of the tissue anchor from a lumen defined by the second needle.

In some embodiments, the coupling a first suture to the tissue anchor includes forming a loop in the suture such that at least a portion of the tissue anchor extends through the loop.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device kit, comprising:
a tissue anchor being configured to be disposed within bodily tissue and having a first arm portion, a second arm portion, and a base portion extending between the first arm portion and the second arm portion;
an elongate member having a cylinder portion defining a lumen along a longitudinal axis of the elongate member, the cylinder portion having a distal end and a proximal end, the proximal end defining an opening;
a first needle extending from the distal end of the cylinder portion, the first needle defining a lumen configured to receive at least a portion of the first arm portion of the tissue anchor, the first needle including a distal end and a proximal end, the first needle having a slot defined by a sidewall of the first needle, the slot extending from the distal end of the first needle to the proximal end of the first needle;
a second needle extending from the distal end of the cylinder portion, the second needle defining a lumen configured to receive at least a portion of the second arm portion of the tissue anchor;
a pusher configured to contact and move the tissue anchor, the pusher including a first portion disposed within the lumen of the cylinder portion and a second portion disposed outside the lumen and a structure of the cylinder portion, the second portion extending from the opening, the first portion and the second portion extending along the longitudinal axis of the elongate member,
the first portion of the pusher includes a projection portion, the projection portion extending laterally from a shaft of the pusher at a location on the shaft that is a distance away from an end of the first portion of the pusher, the projection portion being configured to contact a biasing member to bias the pusher to a retracted position, the biasing member being disposed within the lumen of the cylinder portion between the distal end of the cylinder portion and the projection portion of the pusher; and
an implant having at least one arm member, wherein the at least one arm member is configured to be coupled to the tissue anchor, the implant configured to extend beneath a bladder of a patient to provide support to the bladder.

2. The medical device kit of claim 1,
wherein the pusher is configured to contact and move the tissue anchor such that the first arm portion of the tissue anchor moves from a first location within the lumen defined by the first needle to a second location within the lumen defined by the first needle, and the second arm portion of the tissue anchor moves from a first location within the lumen defined by the second needle to a second location within the lumen defined by the second needle.

3. The medical device kit of claim 1, wherein the pusher includes an elongate portion and a contact portion, the contact portion being disposed on a distal end portion of the elongate portion.

4. The medical device kit of claim 3, wherein the contact portion has a first portion configured to contact the first arm portion of the tissue anchor and a second portion configured to contact the second arm portion of the tissue anchor.

5. The medical device kit of claim 1, wherein the pusher is slideably coupled to the elongate member.

6. The medical device kit of claim 1, wherein the pusher is slideably coupled within the lumen defined by the cylinder portion.

7. The medical device kit of claim 1, wherein the first and second needles are configured to house a plurality of tissue anchors.

8. The medical device kit of claim 1, wherein the second portion of the pusher is configured to receive direct user pressure in order to contact and move the tissue anchor.

9. The medical device kit of claim 1, wherein the base portion is a first base portion, the tissue anchor including a third arm portion, a second base portion, and a third base portion, the second base portion extending between the second arm portion and the third arm portion, the third base portion extending between the third arm portion and the first arm portion.

10. The medical device kit of claim 1, wherein the first arm portion includes an anchor member and the second arm portion includes an anchor member, the lumen of the first needle being configured to receive the anchor member of the first arm portion, the lumen of the second needle being configured to receive the anchor member of the second arm portion.

11. The medical device kit of claim 1, wherein the base portion is unitarily formed with the first arm portion and the second arm portion.

12. The medical device kit of claim 1, wherein the pusher is configured to move in a distal direction based on a force applied to the second portion of the pusher, wherein movement of the pusher results in the biasing member being compressed between the projection portion and the distal end of the cylinder portion.

13. A medical device kit comprising:
a tissue anchor being configured to be disposed within bodily tissue and having a first arm portion, a second arm portion, and a base portion extending between the first arm portion and the second arm portion, the base portion being unitarily formed with the first arm portion and the second arm portion, the tissue anchor including a polymer or plastic material;
an elongate member including a cylinder portion having a longitudinal axis, the cylinder portion defining a proximal end surface, a distal end surface, and a lumen extending from the proximal end surface and the distal end surface along the longitudinal axis, the proximal end surface being disposed in a plane orthogonal to the longitudinal axis of the elongate member, the proximal end surface defining an opening;
a first needle extending from the distal end surface of the cylinder portion, the first needle defining a lumen configured to receive at least a portion of the first arm portion of the tissue anchor, the first needle including a distal end and a proximal end, the first needle having a slot defined by a sidewall of the first needle, the slot of the first needle extending from the distal end of the first needle to the proximal end of the first needle;
a second needle extending from the distal end surface of the cylinder portion, the second needle defining a lumen configured to receive at least a portion of the second arm portion of the tissue anchor, the second needle including a distal end and a proximal end, the second needle having a slot defined by a sidewall of the second needle, the slot of the second needle extending from the distal end of the second needle to the proximal end of the second needle;
a pusher configured to contact and move the tissue anchor, the pusher including a first portion disposed within the lumen of the cylinder portion and a second portion disposed outside the lumen and a structure of the cylinder portion, the second portion extending proximally from the opening of the proximal end surface, the second portion extending linearly from the first portion along the longitudinal axis of the cylinder portion, the first portion of the pusher including a projection portion, the projection portion extending laterally from a shaft of the pusher at a location on the shaft that is a distance distally away from an end of the first portion of the pusher, the projection portion being configured to contact a biasing member to bias the pusher to a retracted position, the biasing member being disposed within the lumen of the cylinder portion between the distal end surface of the cylinder portion and the projection portion of the pusher;

an implant having a plurality of arm members, wherein the plurality of arm members are configured to be coupled to a plurality of tissue anchors including the tissue anchor; and a plurality of sutures, each of the plurality of sutures configured to be looped around only the base portion of the tissue anchor, wherein ends of each of the plurality of sutures are configured to be coupled to at least one arm member of the implant.

14. The medical device kit of claim 13, wherein a structure of the elongate member is completely cylindrical.

15. The medical device kit of claim 13, wherein the pusher is configured to contact and move the tissue anchor such that the first arm portion of the tissue anchor moves from a first location within the lumen defined by the first needle to a second location within the lumen defined by the first needle and the second arm portion of the tissue anchor moves from a first location within the lumen defined by the second needle to a second location within the lumen defined by the second needle.

16. The medical device kit of claim 13, wherein the pusher includes a contact portion disposed on a distal end of the first portion of the pusher, the contact portion defining a first contact portion offset from the longitudinal axis of the cylinder portion and a second contact portion offset from the longitudinal axis of the cylinder portion, the first contact portion configured to contact and move the first arm portion of the tissue anchor, the second contact portion configured to contact and move the second arm portion of the tissue anchor.

17. The medical device kit of claim 13, wherein the second portion of the pusher is configured to receive direct user pressure in order to contact and move the tissue anchor.

18. The medical device kit of claim 13, wherein the pusher is configured to move in a distal direction based on a force applied to the second portion of the pusher, wherein movement of the pusher results in the biasing member being compressed between the projection portion and the distal end surface of the cylinder portion.

* * * * *